United States Patent [19]

Ryan

[11] Patent Number: 5,260,048
[45] Date of Patent: * Nov. 9, 1993

[54] TISSUE FIXATIVE SOLUTION AND METHOD

[75] Inventor: Wayne L. Ryan, Omaha, Nebr.

[73] Assignee: Streck Laboratories, Inc., Omaha, Nebr.

[*] Notice: The portion of the term of this patent subsequent to Mar. 23, 2010 has been disclaimed.

[21] Appl. No.: 877,738

[22] Filed: May 4, 1992

Related U.S. Application Data

[63] Continuation-in-part of Ser. No. 696,926, May 8, 1991, Pat. No. 5,196,182.

[51] Int. Cl.$^5$ .............................................. G01N 1/28
[52] U.S. Cl. ...................................... 424/3; 514/400; 514/727
[58] Field of Search ................ 424/3, 9; 514/400, 727

[56] References Cited

U.S. PATENT DOCUMENTS

| | | | |
|---|---|---|---|
| 4,882,284 | 11/1989 | Kirchanski et al. | 436/63 |
| 5,112,871 | 5/1992 | Austin | 514/727 |
| 5,118,713 | 6/1992 | Donofrio et al. | 514/709 |

*Primary Examiner*—Allen J. Robinson
*Assistant Examiner*—Brian M. Burn
*Attorney, Agent, or Firm*—Tilton, Fallon, Lungmus & Chestnut

[57] ABSTRACT

A tissue fixative solution and method is disclosed which comprises a histological fixing composition of diazolidinyl urea, 2-bromo-2-nitropropane-1,3-diol and a water-soluble zinc salt such as zinc sulfate dissolved in a solvent such as water, alcohol or dimethylsulfoxide. The fixative solution of the invention is much less toxic than prior art fixatives and thus can be used more safely, conveniently and effectively than previous solutions in histological techniques. In addition, the fixative solution allows good tissue preservation to be obtained, and because tissue antigens are retained, the fixative is useful for all types of immunostaining procedures.

25 Claims, No Drawings

TISSUE FIXATIVE SOLUTION AND METHOD

This is a continuation-in-part of U.S. patent application Ser. No. 07/696,926, filed May 8, 1991, now U.S. Pat. No. 5,196,182.

BACKGROUND OF THE INVENTION

The present invention relates to solutions containing compositions useful in the fixation of cells and tissues for histological study and to methods for the fixation of cells and tissues using as the fixing agents certain compounds.

The objective of tissue fixation is to provide as much detail of the cell as possible. To do this, it is necessary to maintain the cells in their original unaltered morphology so that maximum cellular detail is observed under the microscope. With the development of immunostaining there is also the requirement that the antigens of the cells are not altered by the method of fixation or stabilization. Although the microscope is the usual means for examining cells that are fixed and stained, they may also be examined by the laser or the flow cytometer. The flow cytometer is an important device for examining a large number of cells in a brief time.

The usual formulations for stabilization of cells contain one or more agents which react vigorously with the proteins of the cells to denature, coagulate and insolubilize the components of the cell. Typical of this type of agent is formaldehyde, picric acid, mercuric ions and glutaraldehyde. In addition, some less toxic compounds which can also denature and stabilize the proteins are acetic and formic acid, but these are often less suitable for a number of histological procedures.

Unfortunately, the toxicity associated with most of the compounds commonly used in histological techniques renders their use less than satisfactory. For example, formaldehyde, the most common of these fixatives, is a noxious gas which is also toxic, flammable and carcinogenic. Although efforts are made when this chemical is used to protect workers and avoid contamination of the drainage system when disposed, these efforts are usually both expensive and inconvenient, and fixatives such as formaldehyde still present a danger to laboratory workers and health care professionals. It is thus highly desirable to develop fixatives which can be used safely, effectively and conveniently in histological studies.

SUMMARY OF THE INVENTION

Thus, it is an object of the invention to provide a fixative solution for tissues and cells which has extremely low toxicity yet meets all of the requirements of a model fixative.

Another object of the present invention is to provide a fixative which in addition to being low in toxicity gives off no noxious fumes, is not flammable or carcinogenic, and which can be disposed of safely and conveniently when use is completed.

Yet another object of the invention is to provide a fixative solution for tissues and cells that preserves tissues and cells and their antigenic detail to allow for the satisfactory conducting of immunohistochemical and other immunological techniques on the tissues and cells.

A further object of the invention is to provide a fixative solution that provides an unaltered antigenic surface for reaction with specific antibodies.

These and other objects of the invention are obtained by a fixative solution for tissues and cells comprising histological fixing amounts of the following ingredients:
i) diazolidinyl urea;
ii) 2-bromo-2-nitropropane-1,3-diol (also known as "Bronopol"); and
iii) a water-soluble zinc salt in a solvent selected from the group consisting of water, alcohol, dimethylsulfoxide and mixtures thereof. In the preferred embodiment of the invention, the water-soluble zinc salt comprises zinc sulfate. If desired, the above fixative solution can be buffered to a pH of about 4–6 through the addition of a suitable buffer such as a citrate buffer.

In another aspect, the invention comprises an improvement in a method of fixing tissues and cells with a histological fixative wherein the histological fixative is an active agent consisting of:
i) diazolidinyl urea;
ii) 2-bromo-2-nitropropane-1,3-diol (also known as "Bronopol"); and
iii) a water-soluble zinc salt.

Unlike the typical histological fixing agents, the active agents of the invention have extremely low toxicity. For example, toxicity studies comparing diazolidinyl urea of the invention with formaldehyde of the prior art show the following:

|  | Inhalation Toxicity | Dermal Toxicity | LD 50 |
| --- | --- | --- | --- |
| Formaldehyde | 500 mg/Kg | 270 mg/Kg | 800 mg/Kg |
| Diazolidinyl urea | None | 2000 mg/Kg | 2570 mg/Kg |

This reduced toxicity makes disposal and handling less of a problem. In addition, since there is no inhalation toxicity, there are no badge detection devices required as there are for formaldehyde.

Another advantage offered by the active agents of the invention is the fact that they are not flammable and therefore do not present a fire hazard as do many of the prior art fixatives.

The solute in the preparations of the invention may also include any of the other addendum conventionally added to histological fixative preparations. These addendum include mordants, other buffers, penetration increasers, osmotically active substances and nuclear detail improvers and nuclear size increasers.

Examples of suitable mordants are salts with a metal ion having an oxidation state of two or more. Illustrative are zinc, strontium, calcium, barium and chromium salts. Other buffers suitable for the invention include alkali metal phosphate salts such as sodium phosphate and potassium phosphate.

Osmotically active substances that may be included in the formulation of the invention are alkali metal salts such as sodium chloride. In addition, sugars such as the polysaccharides, sucrose, glucose and the like may be employed. Nuclear detail improvers and nuclear size increasers include acetic acid and lithium salts such as lithium chloride. Illustrative of substances which increase the rate of penetration of the fixing agent are dimethylsulfoxide and ethanol.

In the preferred embodiment, the active fixative ingredients described above are dissolved in a suitable solvent such as distilled water, and this solution can then be used as a fixative agent in a number of ways as would be obvious to one skilled in the art. For example, the fixative solution can be used to preserve samples of tissue that are being shipped o carried to an examination site. In this process, small vials or jars that have liquid tight seals are filled with the reagent of the invention, and tissue samples are placed in the reagent-containing vial to preserve the samples until they reach an area where further processing can occur.

Tissues prepared for study using the fixative of the invention can be prepared for histological study in any known conventional manner, such as through the use of paraffin, sectioning equipment, staining, mounting on slides, or other common steps utilized prior to microscopic or other examination. The present invention thus provides a safe, convenient and effective fixative solution which can be utilized in the many known histological procedures that employ such solutions.

The following examples are illustrative of formulations and methods of the invention.

EXAMPLE I

A fixative in accordance with the present invention was prepared having the following formulation:
30 grams of Bronopol
30 grams of Diazolidinyl urea
12 grams of zinc sulfate heptahydrate
2.9 grams of sodium citrate dihydrate
dissolved in 1000 ml distilled water.

This solution was used as a fixative for tissue samples by placing the samples in a vial containing the fixative solution, and holding the sample for about four hours in the fixative. After the tissue has been sufficiently treated with fixative, it is then dehydrated using a series of graded alcohols, cleared in xylene and impregnated with molten paraffin. This procedure is performed under heat and vaccuum/pressure in a 12-hour cycle using a Fisher Histomatic Model 166MP tissue processor. The tissue is then blocked, paraffin embedded, rehydrated in ice water for about three hours to enhance sectioning, and sectioned at 4–5 microns. The tissue is mounted on a glass slide, deparaffinized, stained, coverslipped and evaluated microscopically.

The mechanism by which the active agents of the invention provide the desired tissue and cell membrane is not known for certain. It is believed that the active agent binds in some fashion to the cell membrane or tissue to stabilize. This hypothesis is drawn because many of the active agents of the invention are known disinfectants which kill bacteria by binding to cell structures. This is not a full explanation of the mechanism responsible for the results of the invention since many other disinfectants such as Kathon and Omadine fail to provide tissue and cell stabilizing effects.

The ability of the active agents of the invention to preserve antigens is also not understood but it is probably due to a difference in the reaction between the active agents of the invention and prior art fixatives such as formaldehyde with proteins. Formaldehyde crosslinks with itself and proteins to obscure the antigen. To determine if this is true, diazolidinyl urea was added to the protein albumin to stabilize it. After incubation of diazolidinyl urea and protein mixture for 24 hours, disc-gel electrophoresis indicated no change in the rate of migration of the protein. When this experiment is conducted with formaldehyde, a large number of multimers and insoluble protein results.

DETAILED DESCRIPTION OF THE INVENTION

The fixative solutions of the invention are comprised of histologically effective amounts of the compounds diazolidinyl urea, 2-bromo-2-nitropropane-1,3-diol, and a water-soluble zinc salt such as zinc sulfate in a solvent selected from water, preferably distilled water, alcohol, dimethylsulfoxide and mixtures thereof. The alcohol solvent comprises one or more alkanols such as methanol, ethanol, propanol and butanol; polyols, including diols and triols such as ethylene glycol, glycerol, propylene glycol and trimethylene glycol and mixtures of alkanols and polyols. It is also preferable that a suitable buffer such as a citrate buffer be added to the solution to adjust the pH to about 4–6. One particularly preferred citrate buffer to be used in the solution is sodium citrate dihydrate, but other buffers can be used as would be obvious to one skilled in the art.

The amount of the active agents in the formulation of the invention is that histologically effective amount needed to fix or stabilize the tissue or cell membrane. Generally, the present compositions are preferably about 20–40 grams of Bronopol (about 30 grams particularly preferred), 20–40 grams of diazolidinyl urea (about 30 grams particularly preferred) and about 10–15 grams of the water-soluble zinc salt (about 12 grams particularly preferred) per 1000 ml of solvent used. It is preferred that zinc sulfate, and more particularly zinc sulfate heptahydrate, be employed as the water-soluble zinc salt, but a number of other zinc salts will also be suitable as would be evident to one of ordinary skill in the art. For example, zinc salts such as zinc chloride or zinc acetate could also be employed, but these are considered less effective than zinc sulfate. In addition to the zinc salt, it is preferable to add about 2–6 grams of a citrate buffer (about 3 grams particularly preferred) such as sodium citrate dihydrate to the above fixative solution.

In terms of percentages, it is preferred that the fixative solution comprise about 1–5% Bronopol (about 3% particularly preferred) and about 1–6% diazolidinyl urea (about 3% particularly preferred). In the preferred embodiment, about 0.02 to 0.1 g-mol/L zinc salt (about 0.05 particularly preferred) is added to the fixative solution along with the bronopol and diazolidinyl urea.

Through use of the composition and method of the present invention, satisfactory results have been obtained with a variety of staining methods. The following results have been obtained using the fixative of the invention:

| STAINING METHOD | RESULTS |
| --- | --- |
| Mayer's mucicarmine | Demonstrable; well-defined |
| Elastin | Satisfactory detail |
| Movat's reticulin stain | Satisfactory detail; minimal shrinkage |
| Gomori's trichrome stain | Fibrous tissue well-defined |
| Periodic Acid-Schiff (PAS) | Non-specific staining not evidenced as in formalin-fixed preparation |
| Geimsa | Satisfactory detail |
| Hematoxylin & eosin (H & E) | Satisfactory detail |

EXAMPLE II

The tissue identified below having the antigenic sites identified below are fixed with the fixative formulation of Example I and immunohistochemically stained using avidin-biotin stainings.

| Tissue | Markers Detected |
|---|---|
| Lymph node | LN-1 |
| | LN-2 |
| | LN-3 |
| | LC |
| | L-26 |
| | UCHL-1 |
| | B72.3 |
| Brain | Neurofilament |
| | Glial Fibrillary Acidic Protein |
| | Vimentin |
| Hodgkins node | Ber $H_2$ |
| | Leu $M_1$ |
| Colon | Cytokeratin MAK-6 |
| | Cytokeratin AE1/AE3 |
| | Epithelial Membrane Ag (EMA) |
| Muscle | Desmin |
| | Smooth Muscle Actin |
| Pituitary | S-100 |
| Thyroid | Thyroglobulin |
| Breast | α-lactalbumin |
| | Estrogen Receptors (ERs) |
| | Progesterone Receptors (PRs) |
| Skin | HMB 45 Melanoma |

None of the antigenic sites are affected by the immunostaining.

What is claimed is:

1. A fixative solution for tissues and cells comprising histological fixing amounts of the following compounds:
   i) diazolidinyl urea;
   ii) 2-bromo-2-nitropropane-1,3-diol; and
   iii) a water-soluble zinc salt in a solvent selected from the group consisting of water, alcohol, dimethylsulfoxide and mixtures thereof.

2. A fixative solution according to claim 1 further comprising a citrate buffer.

3. A fixative solution according to claim 2 wherein the citrate buffer comprises sodium citrate dihydrate.

4. A fixative solution according to claim 1 wherein the water-soluble zinc salt is selected from the group consisting of zinc sulfate, zinc acetate and zinc chloride.

5. A fixative solution according to claim 4 wherein the water-soluble zinc salt comprises zinc sulfate.

6. A fixative solution according to claim 5 wherein the water-soluble zinc salt comprises zinc sulfate heptahydrate.

7. A fixative solution according to claim 1 wherein the solution is buffered to a pH of about 4-6.

8. A fixative solution according to claim 1 comprising about 1-5% w/v 2-bromo-2-nitropropane-1,3-diol, about 1-6% diazolidinyl urea and about 0.02 to 0.1 g-mol./L zinc salt.

9. A fixative solution according to claim 8 comprising about 3% w/v 2-bromo-2-nitropropane-1,3-diol, about 3% diazolidinyl urea and about 0.05 g-mol./L zinc salt.

10. A fixative solution according to claim 8 further comprising a citrate buffer.

11. A fixative solution according to claim 1 wherein the solvent is water.

12. A fixative solution according to claim 1 wherein the solvent is an alcohol.

13. A fixative solution according to claim 1 comprising the following ingredients:
   i) about 20-40 grams of diazolidinyl urea;
   ii) about 20-40 grams of 2-bromo-2-nitropropane-1,3-diol; and
   iii) about 10-15 grams of a zinc salt dissolved in about 1000 ml of distilled water.

14. A fixative solution according to claim 13 further comprising about 2-6 grams of a citrate buffer.

15. A fixative solution according to claim 13 comprising the following ingredients:
   i) about 30 grams of diazolidinyl urea;
   ii) about 30 grams of 2-bromo-2-nitropropane-1,3-diol; and
   iii) about 12 grams of a zinc salt dissolved in about 1000 ml of distilled water.

16. A fixative solution according to claim 15 further comprising about 3 grams of a citrate buffer.

17. In a method of fixing tissues or cells by treating same with a histological fixative, the improvement comprising employing as said histological fixative a composition comprising:
   i) diazolidinyl urea;
   ii) 2-bromo-2-nitropropane-1,3-diol; and
   iii) a water-soluble zinc salt.

18. The method according to claim 17 wherein the composition further comprises a citrate buffer.

19. The method according to claim 18 wherein the citrate buffer comprises sodium citrate dihydrate.

20. The method according to claim 17 wherein the water-soluble zinc salt is selected from the group consisting of zinc sulfate, zinc acetate and zinc chloride.

21. The method according to claim 20 wherein the water-soluble zinc salt comprises zinc sulfate.

22. The method according to claim 21 wherein the zinc salt comprises zinc sulfate heptahydrate.

23. The method according to claim 17 wherein the composition is dissolved in a solvent selected from water, an alcohol and mixtures thereof.

24. The method according to claim 23 wherein the composition comprises about 1-5% w/v 2-bromo-2-nitropropane-1,3-diol, about 1-6% diazolidinyl urea and about 0.05 g-mol./L zinc salt.

25. The method according to claim 24 wherein the composition further comprises a citrate buffer.

* * * * *